United States Patent [19]
Barriere et al.

[11] Patent Number: 5,310,900
[45] Date of Patent: May 10, 1994

[54] STREPTOGRAMIN DERIVATIVES AND THEIR PREPARATION

[75] Inventors: Jean-Claude Barriere, Bures-sur-Yvette; Marie-Christine Dubroueucq, Enghien-les-Bains; Maurice Fleury; Martine Largeron, both of Neuilly-sur-Seine; Jean-Marc Paris, Vaires-sur-Marne, all of France

[73] Assignee: Rhone-Poulenc Rorer S.A., Antony, France

[21] Appl. No.: 961,924

[22] PCT Filed: Jul. 18, 1991

[86] PCT No.: PCT/FR91/00590
§ 371 Date: Jan. 4, 1993
§ 102(e) Date: Jan. 4, 1993

[87] PCT Pub. No.: WO92/01691
PCT Pub. Date: Feb. 6, 1992

[30] Foreign Application Priority Data

Jul. 19, 1990 [FR] France .............................. 90 09235

[51] Int. Cl.[5] ................. C07D 471/14; A61K 31/395
[52] U.S. Cl. ................................................... 540/455
[58] Field of Search ................................. 540/455, 456

Primary Examiner—Robert T. Bond
Attorney, Agent, or Firm—Morgan & Finnegan

[57] ABSTRACT

A Streptogramine derivative of formula (I) is disclosed, wherein the symbol Y is a hydrogen atom, a methyl amino or dimethylamino radical, or a protected methylamino radical, and the symbol R represents a methyl or ethyl radical.

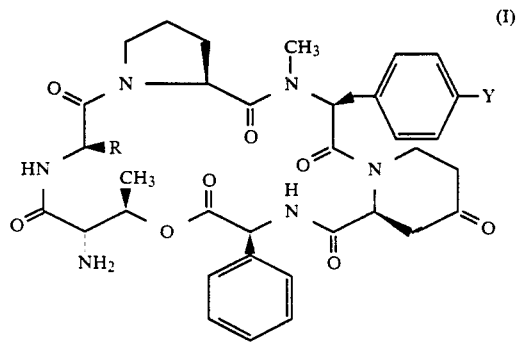

5 Claims, No Drawings

STREPTOGRAMIN DERIVATIVES AND THEIR PREPARATION

FIELD OF THE INVENTION

Streptogramins are known products mentioned, in particular, by J. Preud'homme et al., Bull. Soc. Chim. Fr., 2, 585–91 (1968) or by C. Cocito, Antibiotics, 296 (1983).

In U.S. Pat. No. 4,618,599 and U.S. Pat. No. 4,798,827, soluble derivatives of pristinamycin $I_A$ and of virginiamycin S have been described.

The present invention relates to the preparation of streptogramin derivatives of general formula:

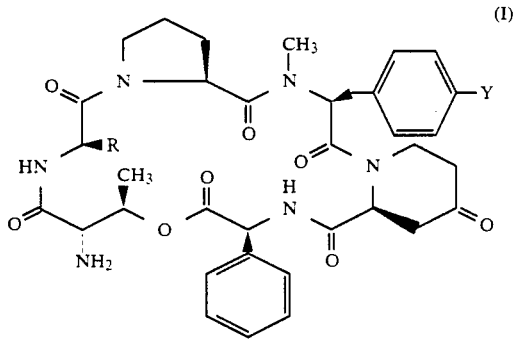

(I)

and to their salts, their preparation [sic] and their use.

BACKGROUND OF THE INVENTION

In the general formula (I), the symbol R represents a methyl or ethyl radical and the symbol Y represents a hydrogen atom or a methylamino or dimethylamino radical or a radical of structure:

(Ia)

in which R' is an amino-protecting radical.

As an example, R' may advantageously be selected from trifluoroacetyl, benzyloxycarbonyl, 2-propenyloxycarbonyl, nitrobenzyloxycarbonyl, 9-fluorenylmethyloxycarbonyl or o-nitrobenzyloxyacetyl.

DESCRIPTION OF THE INVENTION

According to the invention, the streptogramin derivatives of general formula (I) may be obtained by reductive cleavage of a streptogramin of general formula:

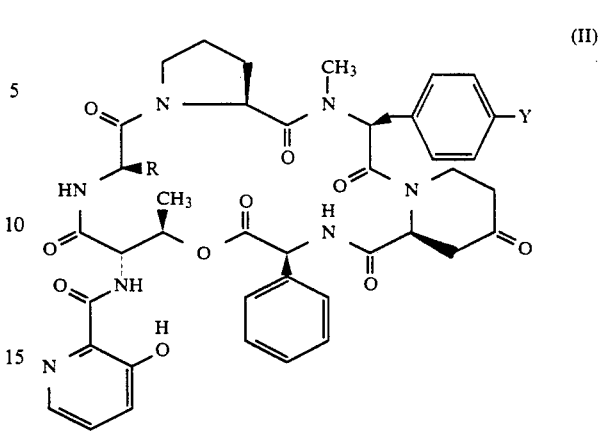

(II)

in which Y and R are defined as above.

The reductive cleavage is carried out by treatment in an acid medium in the presence of a reducing metal.

The reaction is performed in a strong acid medium, at a pH below 2, in the presence of a reducing metal whose redox potential is less than −0.94 V (s.c.e.). The procedure is carried out in an aqueous medium, or in an aqueous-alcoholic medium (for example in a water/methanol or water/ethanol mixture), at a temperature of between −10° and 60° C. The acid may be selected from sulphuric, hydrochloric, hydrobromic, trifluoroacetic or methanesulphonic acid.

As an example, the reducing metal may be advantageously selected from zinc, magnesium, aluminium or sodium amalgam. It is preferable to work under nitrogen.

According to the invention, the streptogramin derivatives of general formula (I) may also be prepared by electrochemical reduction in an acid medium of a streptogramin derivative of general formula (II).

Controlled-potential electrolysis is carried out in aqueous or aqueous-alcoholic acid solution containing up to 50% of alcohol (for example methanol or ethanol), at a temperature of between 0° and 60° C., with constant stirring and under a nitrogen atmosphere, in an electrolysis cell in which the cathode consists of a bed of mercury. The potential of the working electrode E is such that $-0.9 > E > -1.1$ V (s.c.e.).

The acid is advantageously selected from hydrochloric, hydrobromic or sulphuric acid.

The products obtained by the process according to the invention are especially advantageous as intermediates for the preparation of biologically active streptogramin derivatives.

More specifically, they serve as intermediates for obtaining new streptogramin derivatives of general formula:

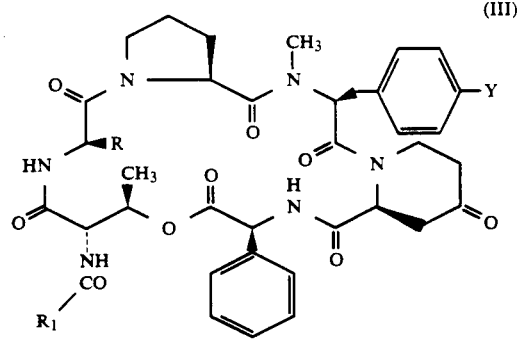

(III)

in which Y and R are defined as above and $R_1$ represents a phenyl or pyridyl radical monosubstituted with a linear or branched alkyl radical containing 2 to 6 carbon atoms or with a trifluoromethyl radical, or represents a phenyl radical disubstituted with linear or branched alkyl radicals containing 1 to 6 carbon atoms or with nitro radicals, or represents a naphthyl radical or a quinolyl radical substituted with a halogen atom, which enable the resistance of tumors to anticancer substances to be eliminated, and are especially advantageous as agents associated with cancer treatment.

The products of general formula (III) may be obtained by the action of an acid of general formula:

$R_1$—COOH  (IV)

in which $R_1$ is defined as above, or a reactive derivative of this acid, on a product of general formula (I).

When a reactive derivative is reacted, the latter may be selected from the anhydride, a mixed anhydride, an acid halide or a reactive ester.

The reaction is performed in an organic medium, optionally in the presence of an acid-acceptor such as a nitrogenous organic base (for, example a trialkylamine, a pyridine, N-methylmorpholine, 1,8-diazabicyclo[5.4.-0]undec-7-ene, 1,5-diazabicyclo[4.3.0]non-5-ene), in an organic solvent such as a chlorinated solvent (for example methylene chloride, dichloroethane, chloroform), an amide (for example dimethylformamide), an oxide (for example dimethyl sulphoxide), a ketone (for example acetone) or an ether (for example tetrahydrofuran), at a temperature of between −20° and 60° C. It is also possible to work in the presence of a condensing agent such as a carbodiimide (for example dicyclohexylcarbodiimide, 1-ethyl-3-(3-dimethylaminopropyl)carbodiimide hydrochloride) and optionally in the presence of a catalyst such as hydroxybenzotriazole, in a solvent mentioned above, or in the presence of an alkali metal carbonate or bicarbonate or alkaline earth metal carbonate or bicarbonate, at the temperature defined above.

The products of general formula (I) or the products of general formula (III) may be purified by known methods such as crystallization or chromatography.

The products obtained according to the invention may be converted to addition salts with acids according to the usual methods. As an example, the salts can be addition salts with inorganic acids, such as hydrochlorides, hydrobromides, sulphates, nitrates or phosphates, or with organic acids, such as acetates, propionates, succinates, maleates, fumarates, methanesulphonates, tartrates, camphorsulphonates or substitution derivatives of these compounds.

The products of general formula (III), prepared from the products according to the invention, are agents capable of maintaining the chemosensitivity of tumors, or of restoring the chemosensitivity of tumors which have become resistant.

Their activity was demonstrated on a doxorubicin-resistant P388 cell line (P388/DOX) [R. K. JOHNSON et al., Canc. Treat. Rep., 62, 1535-1547 (1978)].

On day 0, tubes are inoculated with 3.6 $cm^3$ of a suspension of P388/DOX cells ($2 \times 10^5$ cells/$cm^3$ in RPMI 1640 medium containing 10% of foetal calf serum). The tubes are incubated with the test products at different concentrations and at 37° C. 3 tubes per concentration); the products are solubilized in complete medium and added in a final volume of 0.4 $cm^3$. Another series of tubes is also incubated with the test products at different concentrations, but in the presence of 1 $\mu g/cm^3$ of doxorubicin.

On day 4, the cells are counted. The results are expressed as the $IC_{50}$ ($\mu M$). The $IC_{50}$ corresponds to the concentration of product enabling 50% cytotoxicity due to doxorubicin to be obtained, that is to say at a concentration where the product is not in itself cytotoxic.

In this technique, the products of general formula (III) were shown to be active at concentrations of between 0.2 and 2 $\mu M$.

In addition, the streptogramin derivatives are of low toxicity; they were generally shown to be non-toxic at subcutaneous doses of 200 mg/kg in mice.

EXAMPLES

The examples which follow, given without implied limitation, illustrate the present invention.

In the examples which follow, except where specifically stated, the NMR spectra were recorded at 250 MHz in deuterochloroform; the chemical shifts are expressed in ppm. Flash chromatography is performed under an average pressure of 50 kPa, using a silica of particle size 40-53 $\mu m$, according to W. C. STILL et al., J. Org. Chem., 43, 2923 (1978).

Example 1

200 g of pristinamycin IA are added to 5 liters of 1N aqueous hydrochloric acid solution stirred under a nitrogen atmosphere. A cloudy solution is obtained, the pH of which is in the region of 0.5 and the temperature of which is 27° C. 150 g of powdered zinc are then added in the course of 5 minutes; the temperature of the reaction mixture rises to 32° C. The reaction mixture is stirred for 1 hour at a temperature in the region of 30° C.; the pH of the mixture is then in the region of 1. After the addition of 2 liters of dichloromethane, the pH of the reaction mixture is adjusted to a value in the region of 4 by the slow addition of 110 $cm^3$ of 10N aqueous sodium hydroxide solution. The organic phase is separated after settling has taken place, the aqueous phase is extracted with 500 $cm^3$ of dichloromethane and the combined organic phases are then filtered through a bed of Supercel. The filtrate is washed with 3 times 100 $cm^3$ of distilled water, dried over sodium sulphate, filtered and then concentrated to a volume of 500 $cm^3$ under reduced pressure (2.7 kPa) at a temperature in the region of 30° C. The solution obtained is placed on a column of 7 kg of silica gel (diameter: 15 cm, height: 92 cm). The column is eluted with a dichloromethane/methanol(97:3 by volume) mixture, producing 1.5-liters fractions. Fractions 7 to 13 are concentrated to dryness under reduced pressure (2.7 kPa) at a temperature in the region of 30° C., and the residue obtained is ground for 2 hours in 400 cm³ of pentane, filtered off and then dried under reduced pressure (0.27 kPa) at a temperature in the region of 20° C. 66 g of de(3-hydroxypicolinoyl)-pristinamycin IA are thereby obtained in the form of a white powder, melting at about 206° C.

| δ (ppm) | NMR spectrum: Form | Assignment |
|---|---|---|
| 0.35 | dd | 5 β2 |
| 0.91 | t | 2γ |
| 1.1–1.3 | m | 3 γ2 and 3 β2 |
| 1.38 | d | 1γ |
| 1.52 | m | 3 β1 |
| 1.65 and 1.8 | 2m | 2 β1 and 2β2 |
| 2.02 | m | 3 β1 |
| 2.1 to 2.35 | m | 5 δ2, 5β1 and 5δ1 |
| 2.74 | dt | 5 ε2 |
| 2.87 | s | N(CH$_3$)$_2$ |
| 2.98 | dd | 4 β2 |
| 3.3 | s | NCH$_3$ |
| 3.2 to 3.4 | m | 3 δ2, 4 β1 and 1α |
| 3.52 | m | 3 δ1 |
| 4.6 to 4.9 | m | 3α, 5ε1 and 2α |
| 4.97 | d | 5α |
| 5.24 | dd | 4α |
| 5.75 | q (broad) | 1β |
| 5.83 | d | 6α |
| 6.63 | d | 4ε |
| 7.1 to 7.35 | m | 4δ and aromatic |
| 8 | d | 2 NH |
| 8.63 | d | 6 NH |

Example 2

5 g of powdered zinc are added to a solution, maintained under a nitrogen atmosphere, of 10 g of virginiamycin S1 in a mixture of 200 cm³ of methanol and 50 cm³ of 5N aqueous hydrochloric acid solution. The grey suspension obtained is stirred for 1 hour at a temperature in the region of 20° C. The pH of the reaction mixture is then 1.2; it is thereafter adjusted to 5 by adding 100 cm³ of 1N aqueous sodium hydroxide solution. The mixture is extracted with 3 times 300 cm³ of dichloromethane; the combined organic phases are dried over sodium sulphate, filtered and then concentrated to dryness under reduced pressure (2.7 kPa) at a temperature in the region of 30° C. 8.1 g of residue are thereby obtained, which residue is purified by flash chromatography (eluant: dichloromethane/methanol, 98:2 by volume), collecting 80-cm³ fractions. Fractions 10 to 30 are concentrated to dryness under reduced pressure (2.7 kPa) at a temperature in the region of 30° C. 3.9 g of de(3-hydroxypicolinoyl)virginiamycin S1 are thereby obtained in the form of a white powder, melting at about 175° C.

| δ (ppm) | NMR spectrum: Form | Assignment |
|---|---|---|
| 0.11 | dd | 5 β2 |
| 0.9 | t | 2γ |
| 1.13 | m | 3 γ2 and 3 β2 |
| 1.35 | d | 1γ |
| 1.5 | m | 3 γ1 |
| 1.64 and 1.8 | 2m | 2 β1 and 2 β2 |
| 1.99 | m | 3 β1 and 5 δ2 |
| 2.08 | m | 5 β1 |
| 2.22 | m | 5 δ1 |
| 2.27 | dt | 5 ε2 |
| 3.04 | dd | 4 β2 |
| 3.22 | s | 3 δ2 |
| 3.26 | s | NCH$_3$ |
| 3.3 | m | 1 α |
| 3.38 | m | 4 β1 |
| 3.51 | m | 3 δ1 |
| 1.58 | dd | 3 α |
| 4.65 | m | 5 γ1 |
| 4.75 | dt | 2α |
| 4.97 | d | 5α |
| 5.3 | dd | 4α |
| 5.73 | dq | 1β |
| 5.83 | d | 6α |
| 7.05 to 7.3 | m | aromatic at positions 4 and 6 |
| 8 | d | 2 NH |
| 8.61 | d | 6 NH |

Example 3

Electrolysis is carried out by means of a 3-electrode set-up.

The electrolysis cell consists of an assembly of ground-necked glassware, the anode and cathode compartments being concentric and separated by a porosity 7 sintered-glass wall. A Tacussel PJT 120V-1A potentiostat-galvanostat and a Tacussel IG5 N integrator complete the circuit.

The working electrode is a bed of mercury whose area is equal to 60 cm². The auxiliary electrode is a platinum strip. The reference electrode is a calomel electrode containing saturated potassium chloride solution (s.c.e.).

The electrolysis of a solution of 0.35 g of pristinamycin IA in 200 cm³ of 1N sulphuric acid is performed under a nitrogen atmosphere, at 25° C., over a bed of mercury whose potential is set at −1.0 V s.c.e. At the end of the electrolysis, when the current intensity has become negligible (2 mA) compared with the initial current intensity (120 mA), the pH of the electrolysis solution is taken to around 6.0 by means of 5M potassium carbonate solution. The resulting solution is then extracted with 200 cm³ of dichloromethane. The organic phase is dried over sodium sulphate and concentrated to dryness under reduced pressure (2.7 kPa) at a temperature in the region of 30° C. The residue is taken up with 1 cm³ of dichloromethane and the solution obtained is placed on a column of 15 g of silica gel (diameter: 1.5 cm, height: 60 cm). The column is eluted with a dichloromethane/methanol (98:2 by volume) mixture, collecting 5-cm³ fractions. Fractions 22 to 32 are concentrated to dryness under reduced pressure (2.7 kPa) at a temperature in the region of 30° C. 0.15 g of de(3-hydroxypicolinoyl)pristinamycin IA, the characteristics of which are identical to those of the product obtained in Example 1, is obtained.

Example 4

Using the procedure described above in Example 3, but t a temperature of 10° C., the electrolysis of 0.35 g of pristinamycin I$_A$ is performed. 0.105 g of de(3-hydroxypicolinoyl)pristinamycin IA, the characteristics of which are identical to those of the product obtained in Example 1, is obtained.

Example 5

Using the procedure described above in Example 3, but at a temperature of 40° C., the electrolysis of 0.35 g of pristinamycin $I_A$ is performed. 0.09 g of de(3-hydroxypicolinoyl)pristinamycin IA, the characteristics of which are identical to those of the product obtained in Example 1, is obtained.

Example 6

Using the procedure described above in Example 3, but over a bed of mercury whose potential is set at −0.9 V s.c.e., the electrolysis of 0.35 g of pristinamycin $I_A$, in 200 cm³ of 1N hydrochloric acid is performed. 0.09 g of de(3-hydroxypicolinoyl)pristinamycin IA, the characteristics of which are identical to those of the product obtained in Example 1, is obtained

Example 7

De(3-hydroxypicolinoyl)pristinamycin $I_C$ may be obtained as described in Example 1, but from 1 g of pristinamycin $I_C$, 25 cm³ of 1N aqueous hydrochloric acid solution and 0.5 g of powdered zinc 0.8 g of a residue is thereby obtained, which residue is purified by flash chromatography (eluant:methylene chloride/methanol, 98:2 by volume), collecting 10-cm³ fractions. Fractions 19 to 40 are combined and then concentrated to dryness under reduced pressure (2.7 kPa) at 30° C. 0.3 g of de(3-hydroxypicolinoyl)pristinamycin $I_C$ is thereby obtained in the form of a white powder.

| NMR spectrum | | |
| --- | --- | --- |
| 1.34 | d | $2\beta$ |
| 7.1 to 7.3 | mt | aromatic and $4\delta$ |
| 8.1 | d | >NH at position 2 |
| 8.65 | d | >NH at position 6 |

Example 8

De(3-hydroxypicolinoyl)pristinamycin $I_B$ may be obtained as described in Example 1, but from 1 g of pristinamycin $I_B$, 25 cm³ of 1N aqueous hydrochloric acid solution and 0.5 g of powdered zinc. 0.8 g of a residue is thereby obtained, which residue is purified by flash chromatography (eluant: methylene chloride/methanol, 98:2 by volume), collecting 10-cm³ fractions. Fractions 18 to 36 are combined and then concentrated to dryness under reduced pressure (2.7 kPa) at 30° C. 0.2 g of de(3-hydroxy-picolinoyl)pristinamycin $I_B$ is thereby obtained in the form of a white powder.

| NMR spectrum | | |
| --- | --- | --- |
| 1.6 to 1.9 | mt | $2\beta1$ and $2\beta2$ |
| 1.9 to 2.3 | mt | $5\beta1$, $5\delta1$, $5\gamma2$, $3\beta1$ and $NH_2$ |
| 2.74 | s and mt | $ArNHCH_3$ and $5\epsilon_2$ |

Example 9

De(3-hydroxypicolinoyl)-$N^4$-trifluoroacetylpristinamycin $I_B$ may be obtained as described in Example 2, but from 0.68 g of $N^4$-trifluoroacetylpristinamycin $I_B$, 2.8 cm³ of 5N aqueous hydrochloric acid solution in 14 cm³ of methanol and 0.34 g of powdered zinc in 14 cm³ of methanol.

0.52 g of a residue is obtained, which residue is purified by flash chromatography (eluant:methylene chloride/methanol, 97:3 by volume), collecting fractions of volume 5 cm³ Fractions 6 to 16 are combined and concentrated to dryness under reduced pressure (2.7 kPa) at 30° C. 0.19 g of de(3-hydroxypicolinoyl)-$N^4$-trifluoroacetylpristinamycin $I_B$ is thereby obtained in the form of a white powder. Mass spectrum produced on a VG Autospec apparatus with FAB using a Cs gun in an NBA matrix:

| $(M + H)^+ = 828$ | | |
| --- | --- | --- |
| $(M - H_2O + H)^+ = 810$ | | |
| NMR spectrum | | |
| 1.55 to 1.85 | mt | $3\gamma1$, $2\beta1$ and $2\beta2$ |
| 3.23 and 3.3 | 2s | >N—$CH_3$ at position 4 [ArN($CH_3$)COCF$_3$ + —CO—N($CH_3$)—] |

$N^4$-Trifluoroacetylpristinamycin $I_B$ is obtained in the following manner:

6 mg of trifluoroacetic anhydride are added to 25 mg of pristinamycin $I_B$ dissolved in 1 cm³ of anhydrous dichloromethane. The mixture is left stirring for 12 hours. 6 mg of trifluoroacetic anhydride are added again. The mixture is stirred for 4 hours under reflux, then cooled and adjusted to pH 7-8 with aqueous sodium bicarbonate solution The organic phase is separated off until settling has taken place, and the aqueous phase is washed with twice 2 cm³ of water. The organic phases are combined, dried over sodium sulphate, filtered and then evaporated to dryness under reduced pressure (2.7 kPa) at 30° C. 25 mg of $N^4$-trifluoroacetylpristinamycin $I_B$ are thereby obtained in the form of a white powder.

The products according to the invention may be used in the following manner:

Application Example 1

0.43 cm³ of 4-tert-butylbenzoyl chloride dissolved in 5 cm³ of methylene chloride and 0.34 cm³ of triethylamine are simultaneously added dropwise to a solution, maintained at 5° C., of 1.5 g of de(3-hydroxypicolinoyl)-pristinamycin IA in 25 cm³ of methylene chloride. The reaction mixture is then stirred for 2 hours at a temperature in the region of 20° C. and 20 cm³ of distilled water are thereafter added. The organic phase is separated after settling has taken place, the aqueous phase is extracted twice with 25 cm³ of methylene chloride and the combined organic phases are washed with 20 cm³ of distilled water and then dried over magnesium sulphate. After filtration and then concentration to dryness of the organic phases under reduced pressure (2.7 kPa) at 30° C., 2.2 g of a residue are obtained, which residue is purified by flash chromatography (eluant: ethyl acetate), collecting 10-cm³ fractions. Fractions 8 to 11 are combined and concentrated to dryness under reduced pressure (2.7 kPa) at 30° C. 1.65 g of 1-(4-tert-butylbenzoyl)de(3-hydroxypicolinyl)pristinamycin IA is thereby obtained in the form of a white powder, melting at about 206° C.

NMR spectrum: 0.24 (dd, 5 $\beta2$); 1.34 (s, C(CH$_3$)$_3$); 2 to 2.3 (m, 5 $\delta2$, 5 $\beta1$ and 5 $\delta1$). benzene ring at position 1: 7.57 (d, H3 and H5); 7.88 (d, H2 and H6).

4-tert-Butylbenzoyl chloride may be prepared according to the method described by F. Bell and R .D. Wilson, J. Chem. Soc. 2340 (1956).

Application Example 2

0.42 g of 1-ethyl-3-(3-dimethylaminopropyl)carbodiimide hydrochloride dissolved in 25 cm$^3$ of methylene chloride is added dropwise to a solution, maintained at 5° C., of 1.5 g of de(3-hydroxypicolinoyl)pristinamycin IA, 0.42 g of 3,4-dinitrobenzoic acid and 0.027 g of 1-hydroxybenzotriazole in 35 cm$^3$ of methylene chloride. The reaction mixture is then stirred for 2 hours at a temperature in the region of 5° C., and thereafter for 2 hours at a temperature in the region of 20° C. 20 cm$^3$ of distilled water are added;

The organic phase is separated after settling has taken place, the aqueous phase is extracted twice with 20 cm$^3$ of methylene chloride and the combined organic phases are washed with 20 cm$^3$ of distilled water and then dried over sodium sulphate After filtration and then concentration to dryness of the organic phases under reduced pressure (2.7 kPa) at 30° C., 2.07 g of a residue are obtained, which residue is purified by flash chromatography (eluant: ethyl acetate), collecting 10-cm$^3$ fractions. Fractions 61 to 131 are combined and concentrated to dryness under reduced pressure (2.7 kPa) at 30° C. 1.25 g of 1-(3,4-dinitrobenzoyl)de(3-hydroxypicolinoyl)pristinamycin IA is thereby obtained in the form of a white powder, melting at about 212° C.

NMR spectrum: 0.25 (dd, 5 $\delta$2, 5 $\beta$1 and 5 $\beta$1). 2 to 2.3 (m, 5 $\delta$2, 5 $\beta$1 and 5 $\beta$1). benzene ring at position 1: 8.05 (d, H5); 8.38 (dd, H6); 8.65 (d, H2).

Application Example 3

0.285 cm$^3$ of isobutyl chloroformate is added to a solution, maintained at $-10°$ C., of 0.394 g of 5butylpicolinic acid and 0.22 g of N-methylmorpholine in 20 cm$^3$ of dichloromethane, and the reaction mixture is then stirred for 1 hour at $-10°$ C. A solution of 1.5 g of de(3-hydroxypicolinoyl)pristinamycin IA in 15 cm$^3$ of dichloromethane is then added at $-5°$ C. The mixture obtained is stirred for 16 hours at a temperature in the region of 20° C., and 50 cm$^3$ of distilled water are then added. The organic phase is separated after settling has taken place and washed with 50 cm$^3$ of saturated aqueous sodium chloride solution. After drying over magnesium sulphate, filtration and then concentration to dryness under reduced pressure (2.7 kPa) at a temperature in the region of 30° C., 1.8 g of residue is obtained, which residue is purified by flash chromatography (eluant: 1,2-dichloroethane/methanol, 97:3 by volume), collecting 60-cm$^3$ fractions. The residue obtained after concentration to dryness of fractions 12 to 16 under reduced pressure (2.7 kPa) at a temperature in the region of 30° C. is ground in a mixture of 50 cm$^3$ of ethyl ether and 100 cm$^3$ of pentane. The solid is filtered off and dried at a temperature in the region of 20° C.; 0.75 g of 1-(5-butylpicolinoyl)de(3-hydroxypicolinoyl)pristinamycin IA is thereby obtained in the form of a white powder, melting at 165° C.

NMR spectrum (400 Hz): 0.7 (dd, 5 $\beta$2); 1.04 (t, CH$_3$ of the butyl chain); 1.47 (m, CH$_3$CH$_2$ of the butyl chain); 1.74 (m, CH$_3$CH$_2$CH$_2$ of the butyl chain and 2 $\beta$1); 2.4 (d, 5 $\beta$1); 2.75 to 2.9 (m, CH$_3$CH$_2$CH$_2$CH$_2$ of the butyl chain and 5 $\epsilon$2); pyridine ring at position 1: 7.8 (dd, H4); 8.23 (d, H3); 8.28 (d, H6).

Application Example 4

Using a procedure similar to that described in Example 1, but starting with 1.5 g [lacuna] de(3-hydroxypicolinoyl)pristinamycin IA and 0.37 g of 2,4-dimethylbenzoyl chloride, and after purification by flash chromatography (eluant: 1,2-dichloroethane/methanol, 97.5:2.5 by volume), collecting 30-cm$^3$ fractions, and concentration to dryness of fractions 15 to 19 under reduced pressure (2.7 kPa) at a temperature in the region of 30° C., 0.99 g of 1-(2,4-dimethylbenzoyl)de(3-hydroxypicolinoyl)-pristinamycin IA is obtained in the form of a white powder, melting at about 170° C.

NMR spectrum: 0.21 (dd, 5 $\beta$2); 2.1 (d, 5 $\beta$1); 2.4 and 2.56 (2s, CH$_3$ groups on the benzene ring at position 1) benzene ring at position 1: 7.11 (d(broad), H5); 7.20 (s(broad), H3); 7.48 (d, H6).

Application Example 5

Using a procedure similar to that described in Example 1, but starting with 1.5 g [lacuna] de(3-hydroxypicolinoyl)pristinamycin IA and 0.33 cm$^3$ of 4-trifluoromethylbenzo-yl chloride, and after purification by flash chromatography (eluant: dichloromethane/ethanol, 98:2 by volume), collecting 20-cm$^3$ fractions, and concentration to dryness of fractions 10 to 15 under reduced pressure (2.7 kPa) at a temperature in the region of 30° C., 0.69 g of 1-(4-trifluoromethylbenzoyl)-de(3-hydroxypicolinoyl)pristinamycin IA is obtained in the form of a white powder, melting at about 178° C.

NMR spectrum (400 MHz): 0.25 (dd, 5 $\beta$2); 2.05 to 2.3 (m, 5 $\delta$2, 5 $\beta$1 and 5 $\beta$1); benzene ring at position 1: 7.79 (d, H3 and H5); 8.03 (d, H2 and H6);

Application Example 6

Using a procedure similar to that described in Example 1, but starting with 1.5 g [lacuna] de(3-hydroxypicolinoyl)pristinamycin IA, 0.63 cm$^3$ of triethylamine and 0.91 g of 2-chloro-4-quinolinecarbonyl chloride, and after purification by flash chromatography (eluant: dichloromethane/methanol, 98:2 by volume), collecting 30-cm$^3$ fractions, and concentration to dryness of fractions 10 to 15 under reduced pressure (2.7 kPa) at a temperature in the region of 30° C., 1.02 g of 1-(2-chloro-4-quinolylcarbonyl)-de(3-hydroxypicolinoyl)pristinamycin IA is obtained in the form of a white powder, melting at a temperature above 260° C.

2-Chloro-4-quinolinecarbonyl chloride may be prepared according to the method described by B. Mulert, Chem. Ber., 39, 1901 (1906).

NMR spectrum (400 MHz): $-0.1$ (dd, 5 $\beta$2); 1.97 (d, 5 $\beta$1); quinoline ring-system: 7.91 (s, H3); 7.78, 7.95, 8.18, 8.30 (2t, 2d, H$_5$, H$_6$, H$_7$ and H8).

Application Example 7

Using a procedure similar to that described in Example 1, but starting with 1.5 g [lacuna] de(3-hydroxypicolinoyl)pristinamycin IA and 0.42 g of 1naphthoyl chloride, and after purification by flash chromatography (eluant: ethyl acetate/methanol, 96:4 by volume), collecting 25-cm$^3$ fractions, and concentration to dryness of fractions 12 to 20 under reduced pressure (2.7 kPa) at a temperature in the region of 30° C., 1.06 g of 1-(1-naphthoyl)de(3-hydroxypicolinoyl)pristinamycin IA is obtained in the form of a greenish powder, melting at about 170° C.

NMR spectrum: 0 (dd, 5 $\beta$2); 1.9 to 2.25 (m, 3 $\beta$1, 5 $\beta$1, 5 $\delta$2 and 5 $\delta$1); naphthyl ring-system: 7.5 to 7.8 (m, H3, H6, H7); 7.85 to 8.1 (m, H4, H5, H8); 10 8.46 (d(broad), H2).

Application Example 8

0.21 g of 1-ethyl-3-(3-dimethylaminopropyl)carbodiimide hydrochloride dissolved in 25 cm³ of methylene chloride is added dropwise to a solution, maintained at 5° C., of 0.7 g of de(3-hydroxypicolinoyl)virginiamycin S1, 0.21 g of 3,4-dinitrobenzoic acid and 0.014 g of 1-hydroxybenzotriazole in 20 cm³ of methylene chloride. The reaction mixture is then stirred for 2 hours at a temperature in the region of 5° C., and thereafter for 2 hours at a temperature in the region of 20° C. 20 cm³ of distilled water are added; The organic phase is separated after settling has taken place, the aqueous phase is extracted twice with 20 cm³ of methylene chloride and the combined organic phases are washed with 20 cm³ of distilled water and then dried over sodium sulphate. After filtration and then concentration to dryness of the organic phases under reduced pressure (2.7 kPa) at 30° C., 0.9 g of a residue is obtained, which residue is purified by flash chromatography (eluant: dichloromethane/methanol, 97.5:2.5 by volume), collecting 8-cm³ fractions. Fractions 36 to 60 are combined and concentrated to dryness under reduced pressure (2.7 kPa) at 30° C. 0.5 g of 1-(3,4-dinitrobenzoyl)de(3-hydroxypicolinoyl)virginiamycin S1 is thereby obtained in the form of a white powder, melting at about 190° C.

NMR spectrum: 0.05 (dd, 5 β2); 1.9 to 2.3 (m, 3 β, 5 β2, 5 β1 and 5 δ1); benzene ring at position 1: 8.03 (d, H5); 8 41 (dd, H6); 8.66 (d, H2).

Application Example 9

Using a procedure similar to that described in Example 1, but starting with 1 g [lacuna]de(3-hydroxypicolinoyl)virginiamycin S1, 0.31 cm³ of triethylamine and 0.64 g of 2-chloro-4-quinolinecarbonyl chloride, and after purification by flash chromatography (eluant: dichloromethane/methanol, 98:2 by volume), collecting 10-cm³ fractions, and concentration to dryness of fractions 15 to 35 under reduced pressure (2.7 kPa) at a temperature in the region of 30° C., 0.85 g of 1-(2-chloro-4-quinolylcarbonyl)de(3-hydroxypicolinoyl)virginiamycin S1 is obtained in the form of a white powder, melting at a temperature above 260° C.

NMR spectrum: −0.4 (dd, 5 β2); 2 to 2.2 (m, 5 β2, 5β1 and 5 β1); quinoline ring-system: 7.8 (s, H3); 7.71, 7.93, 8.18, 8.30 (2dt, and d, H5, H6, H7, H8).

Application Example 10

Using the procedure described in Application Example 2, but starting with 0.3 g of de(3-hydroxypicolinoyl)pristinamycin I$_C$, 0.09 g of 3,4-dinitrobenzoic acid, 0.006 g of 1-hydroxybenzotriazole and 0.09 g of 1-ethyl-3-(3-dimethylaminopropyl)carbodiimide hydrochloride, 0.3 g of a residue is obtained, which residue is purified by flash chromatography (eluant: methylene chloride/methanol, 97:3 by volume), collecting 5-cm³ fractions. Fractions 31 to 45 are combined and concentrated to dryness under reduced pressure (2.7 kPa) at 30° C. 0.24 g of 1-(3,4-dinitrobenzoyl)de(3-hydroxypicolinoyl)pristinamycin I$_C$ is thereby obtained in the form of a white powder, melting at about 200°-210° C.

NMR spectrum: 1.26 and 1.32 (2d, 1γ and 2β); 7.10 to 7.4 (mt, aromatic); 8.06 (d, 1'H$_5$); 8.45 (dd, 1'H$_6$): 8.63 (d, >NH at position 1); 8.6 (d, 1'H$_2$); 8.85 (d, >NH at position 6).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for preparing a streptogramin of formula:

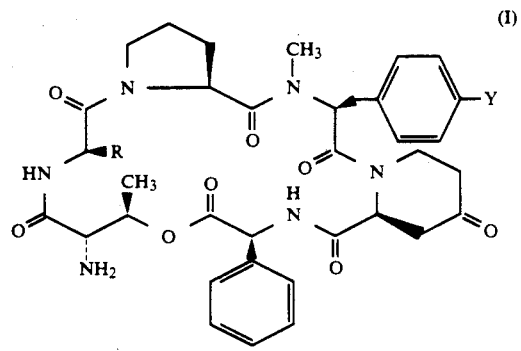

(I)

in which Y is a hydrogen atom or a methylamino or dimethylamino radical or a radical of structure:

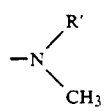

in which R' is an amino-protecting radical and R is a methyl or ethyl radical, comprising the reductive cleavage of a streptogramin of formula:

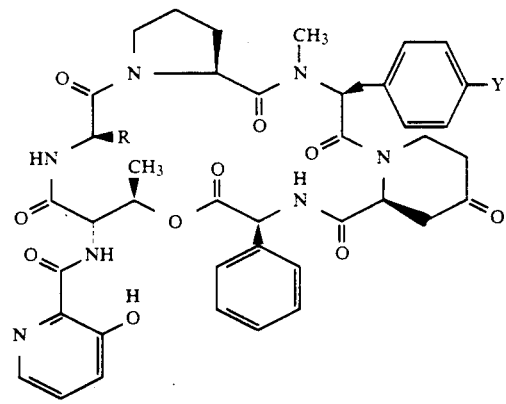

in which Y and R are defined as above, is performed in an acid medium, and the product obtained is then optionally converted to an addition salt with an acid.

2. Process according to claim 1, wherein the reductive cleavage is performed by treatment in an acid medium in the presence of a reducing metal.

3. Process according to claim 1, wherein the reaction is performed in the presence of a reducing metal whose redox potential is less than −0.94 V (s.c.e.).

4. Process for preparing a streptogramin derivative according to claim 1, wherein the reductive cleavage is an electrochemical cleavage in an acid medium of the amide of the streptogramin derivative of formula

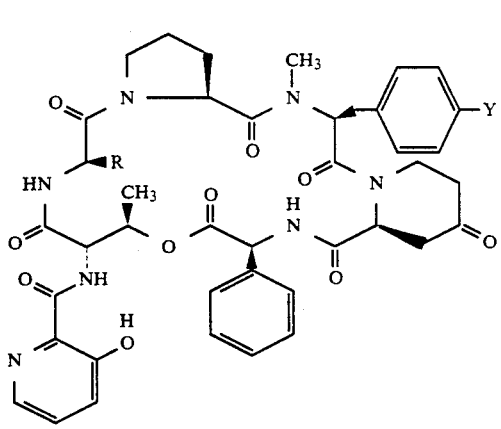

in which Y and R are defined as in claim 1, optionally followed by conversion of the product obtained to an addition salt with an acid.

5. Method for the preparation of a streptogramin derivative of formula:

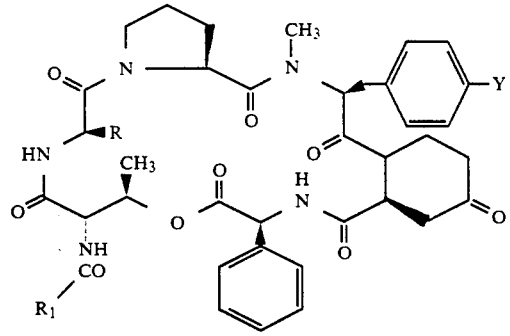

in which R as in claim 1, Y is a hydrogen atom or a methylamino or dimethylamino radical and $R_1$ represents a phenyl or pyridyl radical monosubstituted with a linear or branched alkyl radical containing 2 to 6 carbon atoms or with a trifluoromethyl radical, or represents a phenyl radical disubstituted with linear or branched alkyl radicals containing 1 to 6 carbon atoms or with nitro radicals, or represents a naphthyl radical or a quinolyl radical substituted with a halogen atom comprising using a streptogramin derivative of claim 1.

* * * * *

UNITED STATES PATENT AND TRADEMARK OFFICE
CERTIFICATE OF CORRECTION

PATENT NO. : 5,310,900

DATED : May 10, 1994

INVENTOR(S) : Jean-Claude BARRIERE et al.

It is certified that error appears in the above-identified patent and that said Letters Patent is hereby corrected as shown below:

In the title page:

Change Item [75] Inventor: from "Marie-Christine Dubroueucq"

to read --Marie-Christine Dubroeucq--.

Signed and Sealed this

Twenty-seventh Day of September, 1994

Attest:

BRUCE LEHMAN

*Attesting Officer*  *Commissioner of Patents and Trademarks*